United States Patent
Kulkarni et al.

(10) Patent No.: US 6,365,407 B1
(45) Date of Patent: Apr. 2, 2002

(54) CULTURE MEDIUM COMPOSITION USEFUL FOR INDUCTION AND PROLIFERATION OF TAXUS CALLI

(75) Inventors: Anjali Abhay Kulkarni; Kaza Venkata Krishnamurthy, both of Maharashtra (IN)

(73) Assignee: Council of Scientific & Industrial Research (IN)

(*) Notice: Subject to any disclaimer, the term of this patent is extended or adjusted under 35 U.S.C. 154(b) by 0 days.

(21) Appl. No.: 09/800,447

(22) Filed: Mar. 5, 2001

(51) Int. Cl.⁷ .................................. C12N 5/02
(52) U.S. Cl. ................ 435/430.1; 435/420; 435/422; 435/430
(58) Field of Search .................. 435/430.1, 420, 435/422, 430

(56) References Cited

U.S. PATENT DOCUMENTS

| 5,008,200 A | * | 4/1991 | Rnach et al. | .......... 435/240.49 |
| 5,407,816 A | * | 4/1995 | Bringi et al. | ................ 435/123 |
| 5,843,782 A | * | 12/1998 | Dobres et al. | .............. 435/430 |

* cited by examiner

*Primary Examiner*—Sandra E. Saucier
(74) *Attorney, Agent, or Firm*—Baker Botts LLP

(57) ABSTRACT

Disclosed is a culture composition containing micro and macro-ingredients, vitamins and other supplements such as phytagel, sucrose, picloram. The medium is useful in the formation and development of callus lines of Taxus sp., and resulting in production of taxol in high amounts.

5 Claims, No Drawings

CULTURE MEDIUM COMPOSITION USEFUL FOR INDUCTION AND PROLIFERATION OF TAXUS CALLI

FIELD OF THE INVENTION

The present invention relates to a tissue culture medium composition useful for induction and proliferation of calli from various explants of mature trees of *Taxus baccata* ssp. *Wallichiana* Zucc. Pilg., commonly known as the Himalayan Yew. The invention also relates to a process for production of Taxus plants using the said medium and production of taxane class of anti-cancer compounds in these callus cultures in higher yields.

BACKGROUND OF THE INVENTION

Since the discovery of novel anticancer properties of taxol, a highly derivatized diterpenoid first isolated from *Taxus brevifolia* (Wani et al., J. Am. Chem. Soc. 93: 2325–2327, 1971), considerable interest has been generated about the plants of this genus. All the plant parts from all the species of Taxus are reported to contain taxol and a number of other related taxanes with diverse clinical activities. 10-deacetylbaccatin-III (10-DAB) is one such taxol precursor, which is useful in the semi-synthesis of taxol. The yields of taxol vary from 0.0040% to 0.1% on dry weight basis (Vidensek et al., J. Nat. Prod. 53: 1609–1610, 1990; Witherup et al., J. Nat. Prod. 53: 1249–1255, 1990). The yews have become endangered in their natural habitats because of their over-exploitation and inherent slow growth. Use of plant tissue and cell culture technologies could potentially provide sufficient quantities of taxol and other related, clinically active taxanes for human use, without resorting to the cutting down of the yew trees for extraction of the taxanes.

A number of reports have either been published or patented as listed in the review by Jaziri et al. (Plant Cell Tissue Organ Cult. 46: 59–75, 1996 and references cited therein), related to taxol and/or taxane production in vitro from callus cultures derived from either Pacific or European or Japanese or Korean Yews. *Taxus baccata* ssp. *Wallichiana* Zucc. Pilg., Himalayan Yew is an endangered gymnosperm growing at altitudes of above 3000 m. Not much work has been done on these plants. There are no reports pertaining to taxol and/or 10-DAB production in tissue cultures of the Himalayan Yew except for the paper on the production of 2-deacetoxytaxinine and 2-deacetoxyaustrospicatine from callus cultures of *Taxus wallichiana* (Banerjee et al., Planta Med. 62: 333–335, 1996). The composition of the basic medium published earlier by Gamborg et al. (1968) is as follows:

| Ingredients | Amount (mg·L$^{-1}$) |
|---|---|
| Macronutrients | |
| KNO$_3$ | 2500 |
| MgSO$_4$.7H$_2$O | 250 |
| (NH$_4$)$_2$SO$_4$ | 134 |
| NaH$_2$PO$_4$.H$_2$O | 150 |
| CaCl$_2$.2H$_2$O | 150 |
| Na$_2$-EDTA | 37.2 |
| FeSO$_4$.7H$_2$O | 27.8 |
| Micronutrients | |
| H$_3$BO$_3$ | 3.0 |
| COCl$_2$.6H$_2$O | 0.025 |
| CuSO$_4$.5H$_2$O | 0.025 |
| MnSO$_4$.H$_2$O | 10.0 |
| ZnSO$_4$.7H$_2$O | 2.0 |
| KI | 0.75 |
| Na$_2$MoO$_4$, 2H$_2$O | 0.25 |
| Vitamins | |
| Myo-inositol | 100 |
| Nicotinic acid | 1.0 |
| Pyridoxin.HCl | 1.0 |
| Thiamine.HCl | 10.0 |
| Carbohydrate | |
| Sucrose | 20,000 |

Several patents disclose media and methods for production of taxol from Taxus sp. ex-plants.

The medium compositions described in the prior art are not useful for formation and proliferation of callus lines of Himalayan Yew. Hence, the applicants have developed a novel medium suitable for development of callus lines of Taxus sp. such cultures are capable of producing high amount of Taxol.

OBJECTS OF THE INVENTION

The main object of the present invention is to provide a culture medium for induction and proliferation of callus lines from mature explants of *Taxus baccata* ssp. *Wallichiana* Zucc. Pilg., Himalayan Yew.

Another object of the invention is to provide a method for production of Taxus plants using the culture medium of the invention.

Another object is to provide a process for the production of taxol and 10-DAB from callus cultures of *Taxus baccata* ssp. *Wallichiana* Zucc. Pilg.; which is a native tree of India.

Another objective is to report an optimized culture medium composition for induction and proliferation of callus cultures from a number of explants like stems, needles, embryos and endosperms from mature trees of *Taxus baccata* ssp. *Wallichiana* Zucc. Pilg., Himalayan Yew.

Another objective of the present investigation is to provide a composition of the culture medium including appropriate concentrations of macronutrients, micronutrients, vitamins, plant growth regulators and antioxidants to obtain fast growing callus cultures from selected explants of *Taxus baccata* ssp. *Wallichiana* Zucc. Pilg., Himalayan Yew.

Yet another objective is to provide a composition capable of sustaining the growth of callus cultures and inducing high production of taxane class of molecules under a given set of incubation conditions.

DETAILED DESCRIPTION OF THE INVENTION

Accordingly the present invention provides a novel culture medium for induction and proliferation of callus lines from mature explants of *Taxus baccata* sp. wallichiana Zucc. Pilg., the Himalayan yew. The medium comprises of macro and micro-nutrients and vitamins as mentioned in Table 1 (modified from the prior art) as well as a number of novel chemical ingredients mentioned in Table 2 that have not been used earlier.

TABLE 1

| Ingredients | Amount (mg.L$^{-1}$) |
|---|---|
| Macronutrients | |
| KNO$_3$ | 2528 |
| MgSO$_4$.7H$_2$O | 246 |
| (NH$_4$)$_2$SO$_4$ | 134 |
| NaH$_2$PO$_4$ | 150 |
| CaCl$_2$.2H$_2$O | 150 |
| Na$_2$—EDTA | 37.2 |
| FeSO$_4$.7H$_2$O | 27.8 |
| Micronutrients | |
| H$_3$BO$_3$ | 3.0 |
| CoCl$_2$.6H$_2$O | 0.025 |
| CuSO$_4$.5H$_2$O | 0.025 |
| MnSO$_4$.H$_2$O | 10.0 |
| ZnSO$_4$.7H$_2$O | 2.0 |
| KI | 0.75 |
| Na$_2$MoO$_4$, 2H$_2$O | 0.25 |
| Vitamins | |
| Myo-inositol | 100 |
| Nicotinic acid | 1.0 |
| Pyridoxin.HCl | 1.0 |
| Thiamine.HCl | 10.0 |

And Other Novel and Variable Ingredients as listed in Table 2

TABLE 2

| Novel Ingredients | Amount (mg.L$^{-1}$) |
|---|---|
| Picloram | 0.1–20.0 |
| Sucrose | 10,000–40,000 |
| Phytagel | 2.0–4.0 |
| Antioxidants (Activated charcoal, PVP, Ascorbic acid, individually or mixtures thereof) | 1.0–5.0 |

The new additions in the present invention for example of Picloram aid in both growth and Taxane production. Picloram was not used earlier in the medium as described in the present invention and hence is non-obvious. Media supplemented with Picloram show an enhanced growth rate (1.5–2.0 times) of callus tissues as compared to media supplemented with other auxins reported earlier in the literature. Calli grown in Picloram supplemented media show an enhanced Taxane production (2.0–5.4 times) as compared to calli grown on media supplemented with other auxins reported earlier in the literature. Also the Taxol production is almost 5000 times the in vivo needle tissues in the highest producer callus.

The use of a number of antioxidants together with Picloram is novel and by preventing the phenolic oxidation of the callus, the antioxidant aid in Taxane production by the callus cells as a response to Picloram.

Thus the combination of the modified medium of the present invention with Picloram, Sucrose, Phytagel and Antioxidants is novel and conducive for good callus growth and Taxane production in vitro. The details are described herewith. The present invention also provides a process for the enhanced production of taxol and/or taxane class of molecules in the said callus cultures which comprises inoculating any plant part of the Himalayan yew in the said culture medium for a period of 30 to 60 days in dark and at a temperature ranging between 24–26° C., to obtain the undifferentiated mass of callus culture, extracting the product by conventional solvent extraction methods and analyzing the compounds by HPLC. The stems, needles and seeds (for excision of embryos and endosperms) derived from mature trees of *Taxus baccata* ssp. *Wallichiana* Zucc. Pilg., Himalayan Yew were first washed in soap water for five min. followed by 95% ethanol treatment for one min. The alcohol was washed off with four washes of double distilled water. Surface sterilization was done with 0.1% HgCl$_2$ for 10 min. under vacuum followed by six washes with sterile distilled water. Following this, the explants were inoculated aseptically in pre-sterilized plastic dishes (55-mm diameter) containing the medium of the present invention.

In a feature of the present invention the product may be either a mixture of taxane class of compounds or Taxol or 10-DAB depending upon the parent tree and the hormonal regime.

In another feature the process for preparation of the medium of the invention may be as follows:

The medium was prepared by mixing constituents mentioned in Tables 1 and 2. The pH of the medium was adjusted to 5.8 before autoclaving and 10 ml of medium was poured in each of the pre-sterilized plastic dishes.

Ten pieces of stems and needles (0.5 cm long) and six nos. of embryos and endosperms were inoculated per dish and incubated in dark and at temperatures of 24–26° C. Each treatment had 10 dishes and each experiment was repeated three times every successive year.

Depending on the age of the explant and culture conditions, callus induction occurred in 30–60 days and the subcultures were carried out every four weeks on fresh media in plastic dishes.

The culture medium and method described in the present invention was tested on ex-plants of a number of matures trees (80–100 year old) collected from the Himalayas. The present protocol is applicable to all the ex-plants derived from all these trees of varying ages and genotypes. A series of callus lines were initiated and currently various callus lines of different ages produce the desirable taxanes. A number of callus lines of different ages and derived from diverse parent trees were analyzed by HPLC for detection of taxane class of molecules. Table 3 describes the conditions employed for HPLC analysis. A number of callus lines were found to produce Taxol and/or 10-DAB. For each of the callus lines, extractions were performed at least on three different occasions and duplicate HPLC injections were made on separate days to check for the reproducibility of the results.

TABLE 3

| | |
|---|---|
| System and software | Merck-Hitachi with HSM Manager |
| HPLC column | Lichrosorb RP-18, 5 $\mu$M particle size, 250 × 4.6 mm. |
| Mobile phase | Methanol (65%) : Water (35%) |
| UV detection | 225 nm |
| Injection volume | 20 $\mu$L |

The present invention is described herein below with reference to examples which are illustrative only and should not be construed to limit the scope of the present investigation in any manner.

The following examples illustrate the effects of novel compounds on growth and Taxol content in vitro.

EXAMPLE 1

The formulation and method described in the present invention, with or without antioxidants and containing 4–6 mg.l$^{-1}$ picloram, was tested on tree nos. 1, 3 and 4 from an identified location in the Himalayas. Callus formation was observed in 90% of the ex-plants. Faster growing callus lines were selected from these calli. The callus lines derived from needles of these trees were selected for HPLC analysis. Although the needles used for callus initiation contained 0.0941 μg taxol/g dry weight on an average, callus line 6 contained 500–590 μg taxol/g dry weight, a phenomenal increase (5300–6200 times) as compared to the in vivo material.

EXAMPLE 2

The formulation and method described in the present invention, with or without antioxidants and containing 0.5–2 mg.l$^{-1}$ picloram, was tested on tree nos. 2, 6 and 7 from an identified location in the Himalayas. Callus formation was observed in 90% of the ex-plants. The callus lines derived from needles of these trees contained 190–300 μg taxol/g dry weight as per the HPLC analysis. Since the needles used for callus initiation contained 0.934 μg taxol/g dry weight on an average, the increase of taxol content in vitro is in the range of 203 to 321 times than in vivo material.

EXAMPLE 3

The callus lines derived from needles of tree nos. 1 and 4 were selected for HPLC analysis. Although the needles used for callus initiation did not contain any detectable amount of 10-DAB, callus line 8 contained 2500 μg, 10-DAB/g dry weight, an increase of 2500 times than the in vivo material.

The main advantages of the optimized formulation of the present invention are:

1. The present invention is useful for induction and proliferation of callus cultures derived from a variety of mature explants of the Himalayan Yew.
2. The medium composition described in the present invention is suitable for well-sustained growth of the calli for a period of at least three years.
3. The present invention also describes high production of taxane class of anti-tumor compounds in the same medium which is conducive for growth.
4. As the growth and the production media are identical, the present invention can be gainfully exploited for the development of cell culture methodologies.

We claim:

1. A culture medium for induction and proliferation of callus lines from explants, the culture medium comprising

| | |
|---|---|
| A) Macronutrients in the amounts of: | |
| KNO$_3$ | about 2528 mg · L$^{-1}$ |
| MgSO$_4$.7H$_2$O | about 246 mg · L$^{-1}$ |
| (NH$_4$)$_2$SO$_4$ | about 134 mg · L$^{-1}$ |
| NaH$_2$PO$_4$ | about 150 mg · L$^{-1}$ |
| CaCl$_2$.2H$_2$O | about 150 mg · L$^{-1}$ |
| Na$_2$-EDTA | about 37.2 mg · L$^{-1}$ |
| FeSO$_4$.7H$_2$O | about 27.8 mg · L$^{-1}$; |
| B) Micronutrients in the amount of: | |
| H$_3$BO$_3$ | about 3.0 mg · L$^{-1}$ |
| CoCl$_2$.6H$_2$O | about 0.025 mg · L$^{-1}$ |
| CuSO$_4$.5H$_2$O | about 0.025 mg · L$^{-1}$ |
| MnSO$_4$.H$_2$O | about 10.0 mg · L$^{-1}$ |
| ZnSO$_4$.7H$_2$O | about 2.0 mg · L$^{-1}$ |
| KI | about 0.75 mg · L$^{-1}$ |
| Na$_2$MoO$_4$.2H$_2$O | about 0.25 mg · L$^{-1}$; |
| C) Vitamins in the amounts of: | |
| Myo-inositol | about 100 mg · L$^{-1}$ |
| Nicotinic acid | about 1.0 mg · L$^{-1}$ |
| Pyridoxin.HCl | about 1.0 mg · L$^{-1}$ |
| Thiamine.HCl | about 10.0 mg · L$^{-1}$; and |
| D) Other Ingredients in the amounts of: | |
| Picloram | about 0.1–about 20.0 mg · L$^{-1}$ |
| Sucrose | about 10,000–about 40,000 mg · L$^{-1}$ |
| Phytagel | about 2.0–about 4.0 mg · L$^{-1}$ |
| Antioxidants | about 1.0–about 5.0 mg · L$^{-1}$. |

2. The medium as claimed in claim 1, wherein the ex-plants are selected from the group consisting of stem, needle, embryo and endosperm.

3. The medium as claimed in claim 1, wherein the antioxidants are selected from the group consisting of activated charcoal, PVP, ascorbic acid and mixtures thereof.

4. A method for culturing and producing Taxus plants, said method comprising the steps of inoculating any plant part of Taxus sp. in the the culture medium as claimed in claim 1, for a period of about 30 to about 60 days in dark and at a temperature ranging between about 24–about 26° C., to obtain the undifferentiated mass of callus culture, culturing the calli in conventional media to obtain rooted plants and culturing the rooted plants in the field.

5. A process for the enhanced production of taxol and/or taxane class of molecules in callus cultures which comprises: inoculating any plant part of the Himalayan Yew in the culture medium as defined in claim 1 for a period of about 30 to about 60 days in dark and at a temperature ranging between about 24–about 26° C., to obtain the undifferentiated mass of callus, extracting the product by conventional solvent extraction methods and analyzing the compounds by HPLC for detection of Taxol, 10-DAB or other taxanes.

* * * * *

UNITED STATES PATENT AND TRADEMARK OFFICE
CERTIFICATE OF CORRECTION

PATENT NO. : 6,365,407 B1  Page 1 of 1
DATED : April 2, 2002
INVENTOR(S) : Kulkarni et al.

It is certified that error appears in the above-identified patent and that said Letters Patent is hereby corrected as shown below:

Title page,
Item [54], Title: "CULTURE MEDIUM COMPOSITION USEFUL FOR INDUCTION AND PROLIFERATION OF TAXUS CALLI" should read
-- CULTURE MEDIUM COMPOSITION USEFUL FOR INDUCTION AND PROLIFERATION OF TAXUS BACCATA SSP. WALLICHIANA ZUCC. PILG. CALLI --

Column 5,
Line 46, "comprising" should read -- comprising: --
Line 52, "$MgSO_4.7H_2O$" should read -- $MgSO_4 \cdot 7H_2O$ --

Column 6,
Line 4, "$CaCl_2.2H_2O$" should read -- $CaCl_2 \cdot 2H_2O$ --
Line 6, "$FeSO_4.7H_2O$" should read -- $FeSO_4 \cdot 7H_2O$ --
Line 9, "$CoCl_2.6H_2O$" should read -- $CoCl_2 \cdot 6H_2O$ --
Line 10, "$CuSO_4.5H_2O$" should read -- $CuSO_4 \cdot 5H_2O$ --
Line 11, "$MnSO_4.H_2O$" should read -- $MnSO_4 \cdot 7H_2O$ --
Line 12, "$ZnSO_4.7H_2O$" should read -- $ZnSO_4 \cdot 7H_2O$ --
Line 14, $Na_2MoO_4,.2H_2O$" should read -- $Na_2MoO_4 \cdot 2H_2O$ --
Line 17, "Pyridoxin.HCl" should read -- Pyridocxin·HCl --
Line 18, "Thiamine.HCl" should read -- Thiamine·HCl --
Line 35, "the" (second occurrence) should be deleted Signed and Sealed this Twenty-fourth Day of June, 2003

JAMES E. ROGAN
*Director of the United States Patent and Trademark Office*